United States Patent [19]
Jackels et al.

[11] Patent Number: 5,645,818
[45] Date of Patent: Jul. 8, 1997

[54] DIAGNOSTIC COMPOSITIONS COMPRISING A COMPLEX FORMED BY A NITROGENOUS MACROCYCLIC LIGAND WITH METAL IONS

[75] Inventors: Susan C. Jackels, Winston-Salem, N.C.; Dominique Meyer, Saint-Maur, France

[73] Assignees: Guerbet S.A., Villepinte, France; Wake Forest University, Winston-Salem, N.C.

[21] Appl. No.: 371,893

[22] Filed: Jan. 12, 1995

Related U.S. Application Data

[63] Continuation of Ser. No. 237,914, May 4, 1994, abandoned, which is a continuation of Ser. No. 768,391, Nov. 20, 1991, abandoned.

[30] Foreign Application Priority Data

Mar. 24, 1989 [FR] France ................................. 89 03938

[51] Int. Cl.$^6$ ..................................................... A61K 49/00
[52] U.S. Cl. .......................... 424/9.363; 424/9.42; 534/15; 534/16
[58] Field of Search ............................... 424/9.322, 9.34, 424/9.363, 9.42; 534/15, 16

[56] References Cited

U.S. PATENT DOCUMENTS

| | | | |
|---|---|---|---|
| 4,920,195 | 4/1990 | Kankare et al. | 534/16 |
| 5,057,302 | 10/1991 | Johnson et al. | 424/1.1 |
| 5,059,412 | 10/1991 | Simon et al. | 424/1.1 |
| 5,334,371 | 8/1994 | Gries et al. | 424/9 |
| 5,364,613 | 11/1994 | Sieving et al. | 424/9 |
| 5,373,093 | 12/1994 | Vallarino et al. | 534/15 |
| 5,374,416 | 12/1994 | Rousseaux et al. | 424/2 |
| 5,385,893 | 1/1995 | Kiefer | 514/80 |
| 5,417,960 | 5/1995 | Schaefer et al. | 424/9.363 |
| 5,480,990 | 1/1996 | Kiefer et al. | 540/465 |

FOREIGN PATENT DOCUMENTS 0203047  11/1986  European Pat. Off. .

OTHER PUBLICATIONS

H. Stetter et al., "Darstellung und Komplexbildung von Polyazacycloalkan –N–Essigsäuren", *Tetrahedron*, vol. 37, pp. 767–772, 1981.

Newkome et al., "Octahedral Complexes Derived from a Hexaaza–18–crown–6 Ligand: 3,6,12, 15–Tetramethyl–18{N(2,6)–Pyridino, N–1,2,1]$_2$–coronand–6}", Inorganica, Chimica Acta, 77(1983), L47–L49.

*Primary Examiner*—John Kight
*Assistant Examiner*—Lara Chapman Kelley
*Attorney, Agent, or Firm*—Jacobson, Price, Holman & Stern, PLLC

[57] ABSTRACT

The invention relates to ligands having the formula (I), in which X represents a heterocyclic group, together with the process for their preparation. The invention also concerns mono- or polymetallic complexes formed by said ligands with metallic ions selected from lanthanide ions, transition metal ions, barium ion, bismuth ion, lead ion and the radioisotopes $99m_{Tc}$, $111_{In}$, $90_Y$, $64_{Cu}$ and $169_{Yb}$, as well as salts physiologically acceptable to these complexes. The salts of said complexes can be used as diagnostic and therapeutic agents in magnetic resonance imaging, radiology, in vivo chemical displacement agents and in nuclear medicine.

27 Claims, No Drawings

DIAGNOSTIC COMPOSITIONS COMPRISING A COMPLEX FORMED BY A NITROGENOUS MACROCYCLIC LIGAND WITH METAL IONS

This case was filed under 35 U.S.C. §371 and is the national stage of PCT/FR90/00198, filed Mar. 24, 1989. This is a continuation of application Ser. No. 08/237,914, filed May 4, 1994, now abandoned, which in turn is a continuation of application Ser. No. 07/768,391, filed Nov. 20, 1991, abandoned.

The present invention relates to diagnostic compositions comprising a complex formed by a macrocyclic ligand with metal ions which can be used in particular in magnetic resonance imaging, in radiology using X-rays, and as in vivo chemical shift agents.

Thus, the object of the invention is diagnostic compositions comprising a neutral or anionic, mono- or polymetallic complex formed by a ligand of formula I

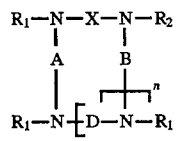

in which

A and B each independently represents a linear or branched $C_1$-$C_8$ alkylene group, a linear or branched $C_1$-$C_8$ hydroxyalkylene group, a linear or branched $C_1$-$C_8$ polyhydroxyalkylene group, a —(CH$_2$—CH$_2$—O)$_z$—CH$_2$—CH$_2$— group, z being an integer from 1 to 3, or at least one of the groups A or B may be represented by the group:

—(CH$_2$)$_p$—CH—
       |
       (CH$_2$)$_q$
       |
       R$_4$ p being equal to an integer from 1 to 7,
q being equal to an integer from 0 to 8, and
R$_4$ representing a group making possible the binding of the macrocycle of formula I to a biomolecule or to a polymer, or a group of formula:

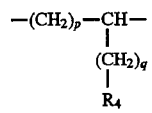

in which
one of the groups A', B' or D' denotes

—(CH$_2$)$_p$—CH—,
       | p being as previously defined,
the other groups A', B' or D' representing A, B or D, respectively,
n is equal to 0 or 1,
D is selected from the groups A, B and a group X, X being selected from the groups

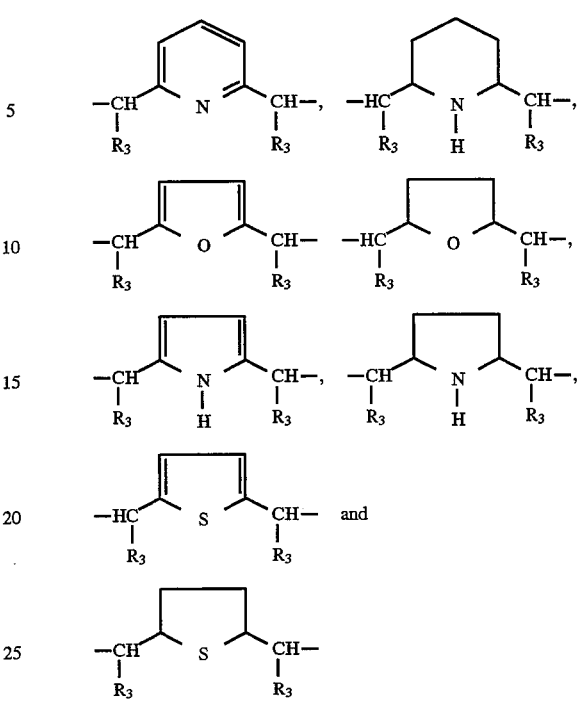

in which
$R_3$ is selected from hydrogen, a $C_1$-$C_5$ alkyl group, a $C_1$-$C_5$ hydroxyalkyl group and a $C_1$-$C_5$ polyhydroxyalkyl group,
$R_1$ is selected from the groups —CH$_2$—COOH and —CH$_2$—PO$_3$H$_2$, and the corresponding anions —CH$_2$COO$^-$ and —CH$_2$—PO$_3^-$,
$R_2$ is selected from hydrogen, a $C_1$-$C_4$ alkyl group, a $C_1$-$C_4$ hydroxyalkyl group, a $C_1$-$C_4$ polyhydroxyalkyl group, a group

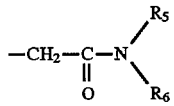

in which
$R_5$ and $R_6$ are each independently selected from hydrogen, a $C_1$-$C_4$ alkyl group, a $C_1$-$C_4$ hydroxyalkyl group and a $C_1$-$C_4$ polyhydroxyalkyl group, the group

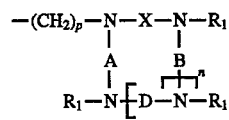

A, B, D, $R_1$ and p being as previously defined as well as the —CH$_2$—COOH and —CH$_2$—PO$_3$H$_2$ groups and the corresponding anions —CH$_2$—COO$^-$ and CH$_2$PO$_2^-$, with metal ions selected from the ions of the lanthanides, the transition metals, barium, bismuth, lead and the radioisotopes: $^{99m}$Tc, $^{111}$In, $^{90}$Y, $^{64}$Cu and $^{169}$Yb, or a salt of this complex with a pharmaceutically acceptable mineral or organic base or a basic amino acid.

A group of ligands forming the complexes is constituted by the compounds of formula I in which:
A represents a linear or branched $C_2$-$C_5$ alkylene group,
B represents a linear or branched $C_2$-$C_5$ alkylene group,
n is equal to 0 or 1, D is selected from a linear or branched $C_2$-$C_5$ alkylene group and a group X, X being selected from the groups:

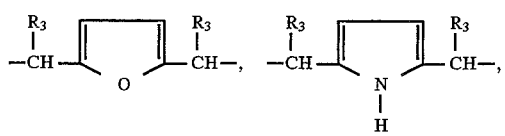

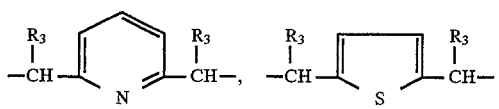

in which $R_3$ is selected from hydrogen and a $C_1$-$C_3$ alkyl group, $R_1$ is selected from the groups —$CH_2$—COOH and —$CH_2$—$PO_3H_2$, and $R_2$ is selected from hydrogen a $C_1$-$C_4$ alkyl group, a $C_2$-$C_4$ hydroxyalkyl group and a group $R_1$ as previously defined.

Another group of ligands forming the complexes is constituted by the compounds of formula I in which n is equal to O and $R_3$ is selected from a $C_1$-$C_5$ alkyl group, a $C_1$-$C_5$ hydroxyalkyl group and a $C_1$-$C_5$ polyhydroxyalkyl group.

Another group of ligands forming complexes is also constituted by the compounds of formula I in which n is equal to 1 and D represents the X group, X being selected from:

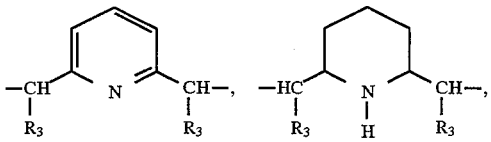

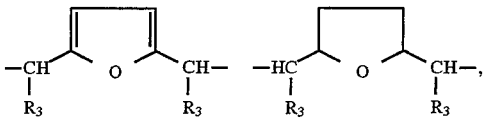

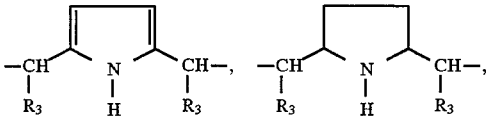

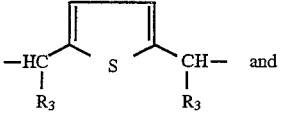

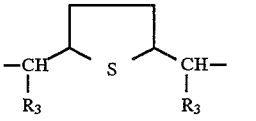

$R_4$ is preferably selected from the groups —$NH_2$, —$CO_2H$,

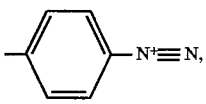

$X^-$, $X^-$ representing a monovalent anion such as $Cl^-$ or $BF_4^-$,

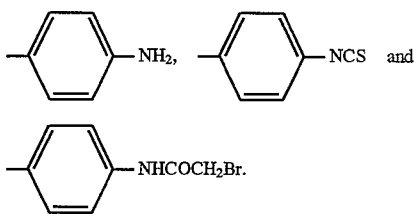

The biomolecules may be proteins, for example albumin or monoclonal antibodies or antibody fragments.

The polymers are selected from peptides, for example, polylysine and the polysaccharides, for example Dextran.

In particular, the ligands constituted by the compounds of formula I in which A and B are identical and selected from the groups ethylene and n-propylene, n is equal to 1, X and D are identical and selected from the following groups, are preferred

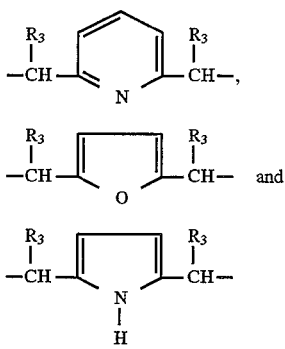

$R_3$ being selected from hydrogen and methyl, and $R_1$ and $R_2$ represent the —$CH_2CO_2H$ group are preferred.

Another group of preferred ligands is constituted by the compounds of formula I in which A and B are identical and selected from ethylene and n-propylene, n is equal to O, X is selected from the groups:

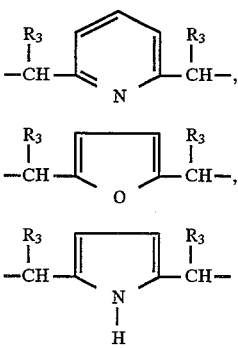

$R_3$ being selected from hydrogen and methyl, $R_1$ represents the —$CH_2CO_2H$ group and $R_2$ represents hydrogen or —$CH_2$—$CO_2H$.

Ligands having the following formulae are among those preferred:

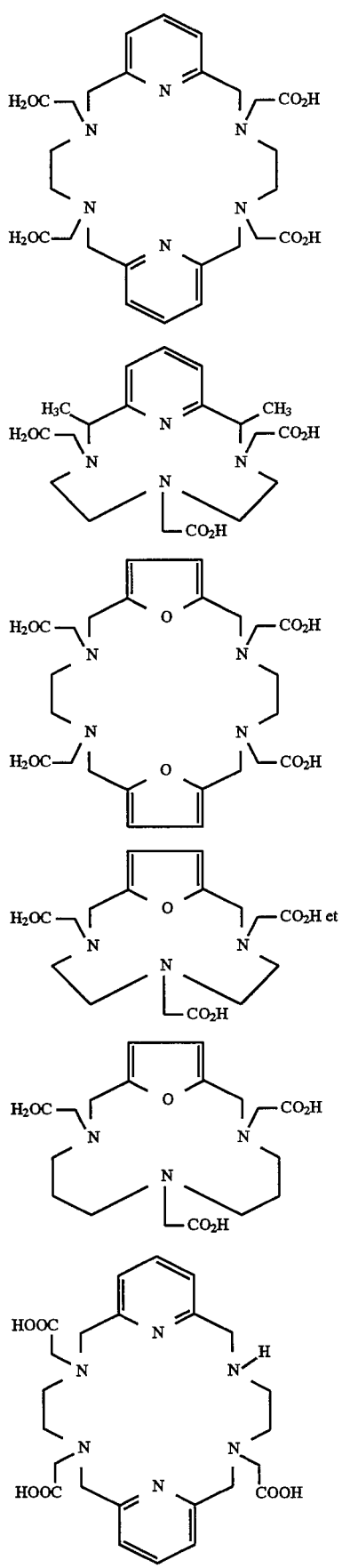
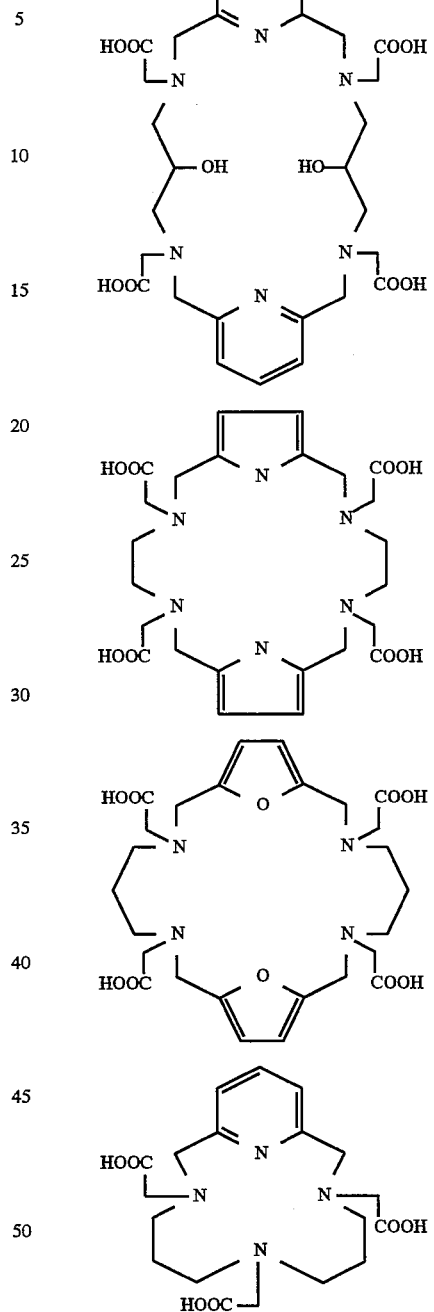
The ligands of formula I may be prepared by reaction of one mole of polyamine of general formula II
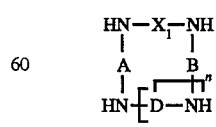
in which A, B and n are as previously defined and D is selected from the groups A, B and a group $X_1$, $X_1$ being selected from the groups:

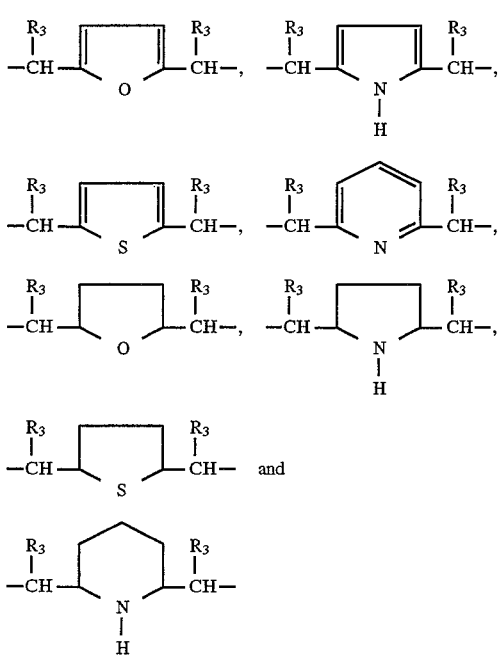

either with 4 moles of a compound of formula III

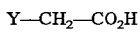
Y—CH$_2$—CO$_2$H in which Y is a labile group such as a chlorine, bromine or iodine atom or a mesyloxy or tosyloxy group, in the presence of sodium or potassium hydroxide when R$_1$ and R$_2$ denote —CH$_2$CO$_2$H, or with 4 moles of formaldehyde in the presence of phosphonic acid when R$_1$ and R$_2$ denote —CH$_2$PO$_3$H$_2$, or with 3 moles of a compound of formula III such as described above in the presence of sodium or potassium hydroxide when R$_1$ represents —CH$_2$CO$_2$H, or with 3 moles of formaldehyde or phosphonic acid when R$_1$ represents —CH$_2$PO$_3$H$_2$, then optionally with one mole of a compound of formula IV

Y—R$_2$ in which Y is as previously defined and R$_2$ is selected from a C$_1$-C$_4$ alkyl group, a C$_1$-C$_4$ hydroxyalkyl group, a C$_1$-C$_4$ polyhydroxyalkyl group, the group

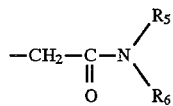

R$_5$ and R$_6$ being as previously defined, and catalytic hydrogenation of the X$_1$ groups is optionally performed in the presence of a suitable metal catalyst such as Pd/C, PtO$_2$, Rh/C, RuO$_2$ under high hydrogen pressure in order to produce the compound of formula I in which X represents a saturated heterocycle (pyrrolidine, piperidine, tetrahydrofuran and tetrahydrothiophene).

The cyclic polyamines of formula II may be prepared by
a) cyclization as described by S. M. Nelson, Pure and Appl. Chem., 52, 2461–2476 (1980), by Fenton, Pure and Appl. Chem. 58, 1437–1444 (1986), by Khalil, K. Abid et al. in Inorganica Chemica Acta, 82 (1984), 223–226, by K. F. Dancey et al. in Synthetic Communications, 16 (7), 795–801 (1986), by V. Mc Kee et al. in J. Chem. Soc., Chem. Commun. 1983, 1465–1467 and by V. Mc Kee et al. in J. Chem. Soc., Chem. Commun., 1985, 158–159, from dicarbonyl compounds of formula V

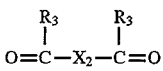

X$_2$ being selected from the groups

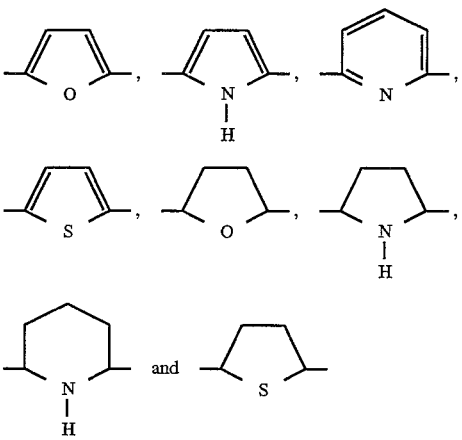

and R$_3$ being as previously defined
with polyamines of formula VI

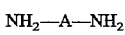
NH$_2$—A—NH$_2$ and VII

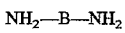
NH$_2$—B—NH$_2$ or with a polyamine of formula VIII

NH$_2$—A—NH—B—NH$_2$

A and B being as previously defined, and
b) reduction of the Schiff base thus obtained by means of a metallic reducing agent such as Na BH$_4$ in a suitable solvent such as methanol to produce the ligands of formula II.

The cyclization reaction takes place optionally in the presence of a metal cation suitable for "cyclization assisted by a metal", the metal being selected from the transition metals, the lanthanides, barium, calcium and strontium in which case the metal cation is removed after cyclization by means of a compound selected from HBr, KCN and H$_2$S.

The compounds of formula II may also be prepared as described in "Darstellung und Komplexbildung von Polyazacycloalkan essig-saüre", H. Stetter et al., Tetrahedron, vol 37, pp. 767 to 772 , 1981 by cyclization of a compound of formula IX

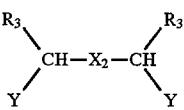

Y being a labile group selected from chlorine, bromine, iodine, the tosyloxy or mesyloxy group obtained from the corresponding alcohols with a polysulfonamide of formula X:

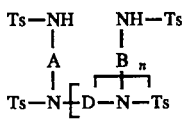

in which Ts is a tosyl group and A, D, B and n are as previously defined, in the presence of a suitable base selected from NaH, MeONa, EtONa and $Cs_2CO_3$ in a suitable solvent such as dimethylformamide and dimethylacetamide or other aprotic solvents or in the presence of a phase transfer catalyst under the conditions of phase transfer known to the prior art.

The complexes are neutral or anionic mono- or polymetallic, and preferably mono- or bi-metallic.

In these complexes, the metal ions are preferably gadolinium, europium, dysprosium, iron ($Fe^{3+}$), manganese ($Mn^{2+}$) and barium.

A preferred bimetallic complex is that formed with a ligand of formula I in which X and D represent the group:

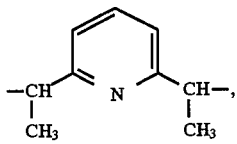

A and B represent the 2-hydroxy propylene group n=1 and $R_1$ and $R_2$ represent —$CH_2$—$COO^-$ with two $Mn^{2+}$ ions.

Examples of salts are those formed with sodium hydroxide, N-methylglucamine, diethanolamine, lysine and arginine.

The complexes may be obtained by reaction of the ligands with a salt or an oxide of the metals in an aqueous solvent and neutralization, if necessary, to form a salt.

It is obvious that the present invention encompasses not only the use of the previously defined complexes in the form of racemic mixtures but also the use of the stereoisomers of these complexes.

The complexes formed by the ligands of formula I may be used for in vitro and in vivo diagnostic purposes in man and animals.

In magnetic resonance imaging and in in vivo NMR spectroscopy they may be used as relaxation agents; for this purpose the complexes formed with the following metals are preferred: $Gd^{3+}$, $Mn^{2+}$ and $Fe^{3+}$; as magnetic susceptibility agents: for this purpose the complexes formed with the metals $Dy^{3+}$, $Ho^{3+}$, $Tb^{3+}$ and $Er^{3+}$ are preferred; or chemical shift agents: for this purpose, the complexes formed with the metals $Eu^{3+}$, $Pr^{3+}$ and $Yb^{3+}$ are preferred.

The complexes formed by the ligands of formula I and the metals selected preferably from $Gd^{3+}$, $Er^{3+}$, $Dy^{3+}$, $Tb^{3+}$, $Ce^{3+}$, $La^{3+}$, $Bi^{2+}$, $Ba^{2+}$ and $Pb^{2+}$ may be used in X-ray imaging.

In nuclear medicine, the complexes formed by the ligands of formula I and the metals $^{99m}Tc$, $^{111}In$, $^{64}Cu$ and $^{169}Yb$ may be used for radiodiagnostic purposes and the complexes formed with the metals $^{90}Y$, $^{212}Bi$ and $^{64}Cu$ may be used for radiotherapeutic purposes after coupling of the complex to a suitable biomolecule.

The complexes formed by the ligands of formula I and the metal ions selected preferably from $Eu^{3+}$ and $Tb^{3+}$ may be used in in vitro diagnostic applications using photoluminescence, such as immunofluorescence assays.

The compositions according to the invention may be constituted in particular by solutions of a complex according to the invention in a physiologically acceptable aqueous solvent.

The diagnostic compositions according to the invention may be administered:

by the parenteral route, including the intravenous route, the intra-arterial route, the intra-lymphatic route and the subcutaneous route by the oral route by the sub-arachnoidal route by the intrabronchial route in the form of an aerosol.

In magnetic resonance imaging, the doses are very variable depending on the route of administration.

In the case of the intravenous or intra-arterial route, the dose is about 0.01 to 2 mM/kg.

In the case of the oral route, this dose may range up to 10 mM/kg.

For the other routes of administration, the useful doses are usually lower than 1 mM/kg and even for the sub-arachnoidal route are usually less than 0.05 mM/kg.

The doses are the same for their use as chemical shift agents for in vivo spectroscopy, as magnetic susceptibility agents in MRI and as contrast agents in radiology using X-rays, except by the intravenous or intra-arterial route in which the doses may be from 0.2 to 5 mM/kg.

The following examples illustrate the preparation of the compounds according to the present application.

In these examples:

the NMR spectra were performed on a Varian EM 360 apparatus at 60 MHz with TMS as internal standard.

EXAMPLE 1

Preparation of the compound of formula:

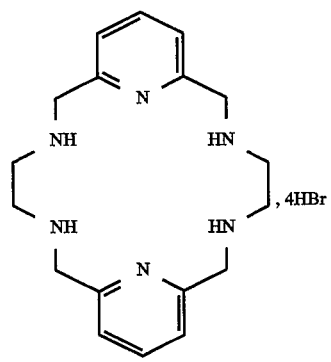

A solution of 1,2-diaminoethane (0.03 mole) in 20 cm³ of methanol is added dropwise to a solution of diformyl pyridine (4.05 g, 0.03 mole) and $BaCl_2.2H_2O$ (3.66 g, 0.015 mole) in 150 cm³ of methanol and the reaction mixture is heated at reflux for 3 hours.

After the solution has been cooled to 0° C., a first portion of $NaBH_4$ (0.08 mole) is added slowly, a second addition of $NaBH_4$ (0.04 mole) is made 30 minutes later.

The reaction mixture is stirred for 1 hour 30 at room temperature, concentrated to dryness and extracted with $CHCl_3$.

The oil obtained after evaporation is recrystallized from methanol in the form of the tetrahydrobromide.

Yield=7.8 g (80%)

NMR in $D_2O$: 7.34 ppm (triplet, J=8 Hz, 6.87 ppm (doublet, J=8 Hz), 3.95 ppm (singlet), 3.24 ppm (singlet).

EXAMPLE 2

Preparation of the compound of formula:

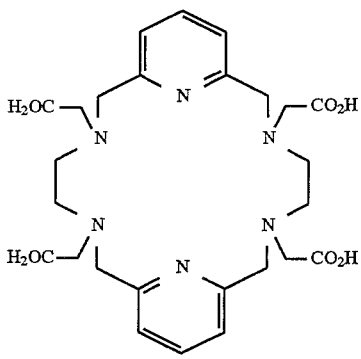

2

A solution of sodium hydroxide (1.17 g in 3 cm$^3$ of H$_2$O) is added to a suspension of 1 (4.77 g, 0.007 mole) in 10 cm$^3$ of water while the temperature is maintained at 25° C.

15.28 g of bromoacetic acid, 9.53 g of 1 and a solution of sodium hydroxide (6.75 g in 17 cm$^3$ of H$_2$O) are then added alternately in small portions during a period of one hour. The temperature is maintained below 60° C. After the addition, the reaction medium is adjusted to pH=8.5 by the addition of sodium hydroxide (4.5 g in 10 cm$^3$ of H$_2$O) and maintained at 45° C. for 36 hours.

The reaction mixture is then adjusted to pH=3 by the addition of HBr, then chromatographed on a resin (Dowex 50×4-400).

After the resin has been washed with water, the product is eluted with a 0.5M solution of ammonia.

The fractions containing the product are adjusted to pH2 by the addition of concentrated HCl and evaporated to dryness. 15.4 g of product are recovered in a yield of 94%.

$^1$H NMR in D$_2$O: 7.54 ppm (triplet J=8 Hz) 7.04 ppm (doublet J=8 Hz), 4.02 ppm (singlet), 3.15 ppm (singlet), 2.98 ppm (singlet).

EXAMPLE 3

Preparation of the sodium salt of the Gd$^3$ complex of the compound of formula 2.

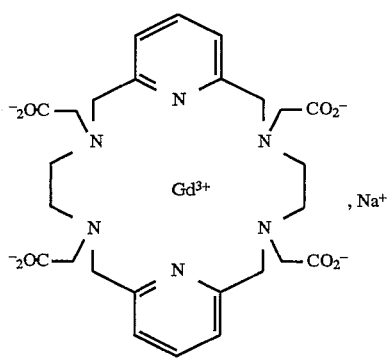

3

The suspension of 0.3625 g of Gd$_2$O$_3$ and 1.557 g of compound 2 in 10 cm$^3$ of H$_2$O is heated at reflux for 4 hours. After being cooled to room temperature, the clear solution is neutralized by the addition of sodium hydroxide to pH 7.2. On addition of acetone (150 cm$^3$), 1.2 g of a white solid are recovered. The complex obtained is recrystallized by dissolution in a water/ethanol (40/60) mixture and addition of acetone.

Elementary analysis—calculated for NaGdC$_{26}$H$_{31}$N$_6$O$_{8.5}$: C 41.95; H 4.17; N 11.29; Gd 21.14. Found: C 42.15; H 4.30; N 11.25; Gd 20.47.

EXAMPLE 4

Preparation of the compound of formula:

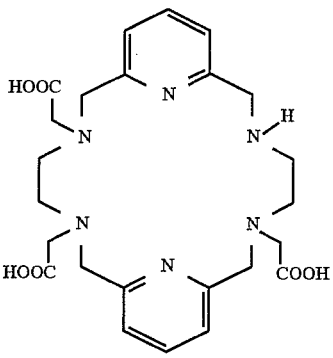

5

A solution of NaOH (60 mmoles, 2.6 g in 10 ml H$_2$O) is added slowly with stirring to a suspension of the compound obtained in example No. 1 (15 mmoles, 9.75 g) in water (30 ml) while the temperature is maintained at about 40° C. by means of a water-bath.

The mixture is stirred while solid BrCH$_2$COOH (15 mmoles, 2.085 g) is added. The pH is maintained at about 8.5 by the continuous addition of a NaOH solution (90 mmoles, 3.6 g in 10 ml H$_2$O) and the temperature is maintained at 60° C. throughout the reaction.

After about 3 hours, 15 mmoles (2.09 g) of solid BrCH$_2$COOH are again added and after a further 4 hours the final quantity (15 mmoles, 2.09 g) of solid BrCH$_2$COOH is added. During these additions, the pH is maintained at 8.5 and the temperature at 60° C.

After 24 h, the pH of the reaction mixture is adjusted to 3.0 by the addition of concentrated HBr.

The salts and excess reagents are removed from the product by cation exchange chromatography (Dowex 50×8).

The reaction mixture is loaded onto the column equilibrated and washed with water until the eluate no longer gives a positive reaction to halides and the pH is about 4.5.

The ligand is eluted from the column with 0.5 molar aqueous NH$_3$. The fractions having a pH of 4.1 to 5.1 are pooled and evaporated to dryness under reduced pressure (yield 6.0 g, 80% of crude product).

The solid is dissolved in 60 ml of CH$_3$OH and added dropwise to a stirred volume of acetone (500 ml) in order to give a very fine white solid.

The solid is recovered and dried in a vacuum at room temperature.

EXAMPLE 5

Preparation of the complex of formula:

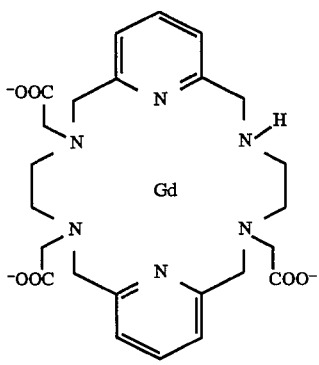

Gd$_2$O$_3$ (2.88 g, 8 mmoles) and the crude compound obtained in the previous example (evaporated eluate obtained from the ion exchange column, 7.96 g (16 mmoles) are suspended in 100 ml of H$_2$O at 80° C. and stirred for 24 hours. During this time the solution becomes clear.

The solution is cooled to room temperature, then the solvent is removed under reduced pressure.

The resultant solid is dissolved in 15 ml of H$_2$O and 5 ml of C$_2$H$_5$OH and the solution is added dropwise to 750 ml of vigorously stirred acetone.

The fine, whitish precipitate which is formed is filtered off, then washed with acetone and dried in a vacuum at room temperature.

Yield: 6.8 g (66%).

EXAMPLE 6

Preparation of the compound of formula:

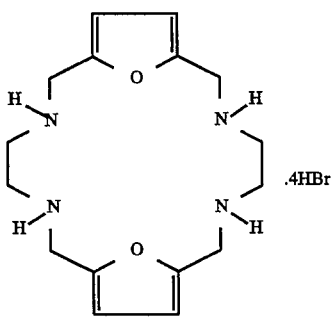

A solution of 1,2-diaminoethane (0.270 ml, 4 mmoles in 40 ml MeOH) is added dropwise to a solution of 2,5-furandicarbaldehyde (0.505 g, 4 mmoles) and Ba(SCN)$_2$·3H$_2$O (0.615 g, 2 mmoles) in 60 ml MeOH during 15 minutes.

The mixture is stirred for 3 hours and the colour turns orange-yellow.

The mixture is then cooled in an ice-bath while NaBH$_4$ (0.404 g, 10.7 mmoles) is added slowly.

The colour of the reaction turns lemon yellow.

After stirring has been continued for 30 minutes, a further addition of NaBH$_4$ (0.2018 g, 5.35 mmoles) is made.

After being stirred for 2 hours at room temperature, the mixture is evaporated to dryness under reduced pressure and the residue (a mixture of white and yellow solids) is extracted five times with 25 ml aliquots of CHCl$_3$.

The pooled chloroform extracts are filtered and evaporated under reduced pressure to give a yellow oil.

The oil is dissolved in MeOH (10 to 15 ml) and HBr (6 to 7 drops of a 48% aqueous solution) is added dropwise to this solution. The product precipitates in the form of a pale yellow solid.

The product is recovered, then dried in a vacuum at room temperature.

Yield: 0.6 g or 42%

Elementary analysis for C$_{16}$H$_{31}$N$_4$O$_{3.5}$Br$_4$: calculated: C, 29.33; H 4.77; N, 8.55; Br, 48.79. Found: C, 29.24; H, 4.81; N, 8.56; Br, 48.00.

EXAMPLE 7

Preparation of the compound of formula:

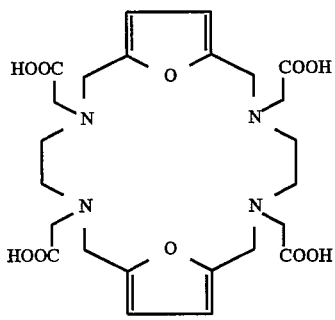

A solution of NaOH (1.6 g, 0.04 mole in 20 ml of H$_2$O) is added slowly with stirring to a suspension of the compound obtained in the previous example (0.01 mole, 6.28 g) in water (30 ml) while the temperature is maintained at about 30° by means of a water-bath.

The mixture is stirred while solid BrCH$_2$COOH (0.02 mole, 2.78 g) is added. The pH is maintained at about 8.5 by the continuous addition of a NaOH solution (3.2 g in 10 ml H$_2$O) and the temperature is maintained at 60° C. throughout the reaction.

After about 3.5 hours, a further addition of about 0.010 mole (1.39 g) of solid BrCH$_2$COOH is added and after a further 3.5 hours, the final quantity (0.010 mole, 1.39 g) of solid BrCH$_2$COOH is added. During these additions, the pH was 8.5 and the temperature was maintained at 60° C.

After 24 hours, there is no further uptake of the NaOH solution and the reaction is stopped. The pH of the reaction mixture is adjusted to 2.7 by addition of concentrated HBr.

The salts and excess reagents are removed from the product by cation exchange chromatography (Dowex 50×8).

The reaction mixture is loaded onto the column equilibrated and washed with water until the eluate no longer gives a positive reaction to halide and the pH is about 4.5.

The ligand is eluted from the column with 0.5M aqueous NH$_3$. The fractions having a pH equal to 3.2 are pooled and evaporated to dryness under reduced pressure (yield 2.7 g).

The solid is dissolved in 15 ml of CH$_3$OH and added dropwise to 200 ml of vigorous stirred acetone to give a very fine white solid.

The solid is recovered and dried in a vacuum at room temperature.

Yield: 1,8 g, 50%.

Elementary analyis for C$_{24}$H$_{33}$N$_4$O$_{10.5}$; Calc. C, 52.84; H, 6.10; N, 10.27. Found: C, 53.06; H, 6.18; N, 9.67.

EXAMPLE 8

Preparation of the complex of formula:

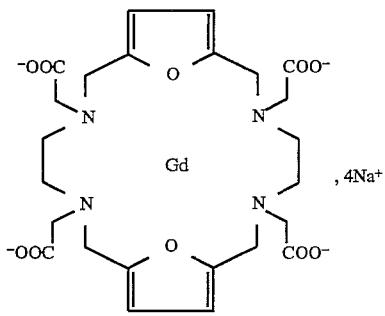

Gd$_2$(CO$_3$)$_2$ (0.3 g, 0.6 mmole) and the compound obtained in the previous example (0.64 g, 1.2 mmole) are suspended in 40 ml of H$_2$O at room temperature and stirred for 48 hours.

The suspension is filtered to give a colourless solution which is neutralized to pH 7 with a NaOH solution (0.05 g in 5 ml of H$_2$O). The solvent is removed under reduced pressure.

The resultant solid is dissolved in 5 ml of H$_2$O and 5 ml of C$_2$H$_5$OH and the solution is added dropwise to 200 ml of vigorously stirred acetone.

The fine white precipitate which is formed is recovered by filtration at a water pump, washed with acetone and dried in a vacuum at room temperature.

Yield: 0.56 g (65%).

EXAMPLE 9

Preparation of the compound of formula:

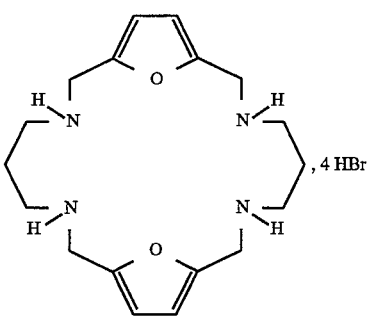

A solution of 1,3-diaminopropane (0.340 ml, 4 mmoles in 40 ml MeOH) is added dropwise and with stirring to a solution of 2,5-furandicarbaldehyde (0.505 g, 4 mmoles) and Ba(SCN)$_2$.3H$_2$O (0.615 g, 2 mmoles) in 60 ml of MeOH during 15 mn.

The mixture is stirred for 20 mn and the colour turns orange-yellow.

The mixture is then cooled in an icebath while NaBH$_4$ (0.404 g, 10.7 mmoles) is added slowly.

The colour of the reaction turns lemon yellow.

After stirring has been continued for 30 mn, a further addition of NaBH$_4$ (0.2018 g, 5.35 mmoles) is made.

After being stirred for 2 hours at room temperature, the mixture is evaporated to dryness under reduced pressure and the residue (a mixture of white and yellow solids) is extracted four times with 15 ml aliquots of CHCl$_3$.

The pooled chloroform extracts are filtered and evaporated under reduced pressure to give an orange oil.

The oil is dissolved in methanol (10 to 15 ml) and HBr (6 to 7 drops of a 48% aqueous solution) is added dropwise to this solution. The product precipitates in the form of a pale yellow solid.

The product is filtered off and dried in a vacuum at room temperature.

Yield: 0.67 g, 50%.

Elementary analysis: calculated for C$_{18}$H$_{32}$N$_4$O$_2$Br$_4$: C, 32.95; H, 4.92; N, 8.54; Br, 48.74. Found: C, 33.04; H, 4.96; N, 8.36; Br, 48.28.

EXAMPLE 10

Preparation of the compound of formula:

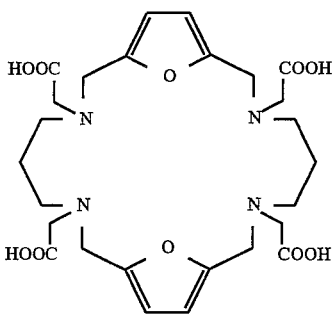

This compound is prepared according to the procedure described in the examples 2 and 7.

EXAMPLE 11

Preparation of the compound of formula:

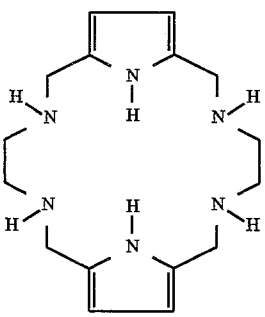

A solution of 1,2-diaminoethane (0.48 g, 8 mmoles in 20 ml MeOH) is added dropwise and with stirring to a solution of 2,5-pyrrole dicarbaldehyde (1.00 g, 8 mmoles) and BaCl$_2$.2H$_2$O (0.976 g, 4 mmoles) in 150 ml of methanol during 15 mn.

The initially yellow solution turns orange during the addition of the ethylenediamine. The mixture is heated at reflux for 3 hours and the colour turns dark brown.

The mixture is then cooled in an icebath while NaBH$_4$ (0.805 g, 21.3 mmoles) is added slowly. The reaction becomes light brown on forming a white precipitate.

After stirring has been maintained for 30 mn, a further addition of NaBH$_4$ (0.404 g, 10.7 mmoles) is made.

After being stirred for 1.5 hour at room temperature, the mixture is evaporated to dryness under reduced pressure and the residue (a mixture of an orange oil and a white solid) is extracted four times with 75 ml aliquots of CHCl$_3$.

The pooled chloroform extracts are filtered and evaporated under reduced pressure to give an orange oil.

The oil is dried in a vacuum at room temperature to give a light brown solid.

Yield: 49%.

$^1$H NMR in CDCl$_3$: 10.08 ppm (large singlet, 2H, pyrrole NH), 5.95 ppm (singlet, 4H, pyrrole CH), 3.80 ppm (singlet, 8H, CH$_2$), 2.70 ppm (singlet, 8H, CH$_2$).

EXAMPLE 12

Preparation of the compound of formula:

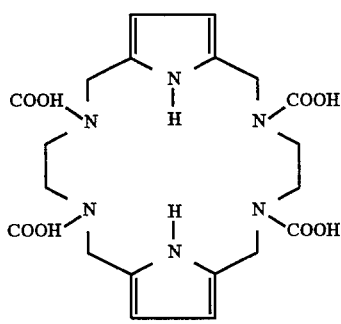

This compound is prepared according to the procedure described in the examples 2 and 7.

EXAMPLE 13

Preparation of the complex of formula:

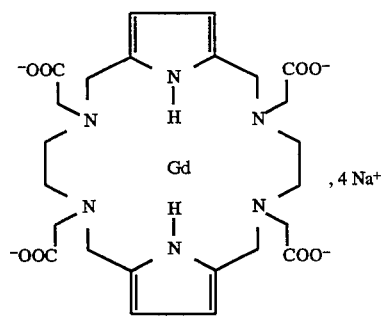

This complex is prepared according to the procedure described in the foregoing examples 3 and 5.

EXAMPLE 14

Preparation of the compound of formula:

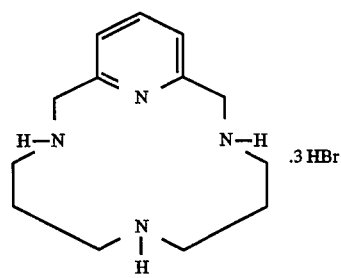

A solution of iminobis (propylamine) (1.4 ml, 0.01 mole in 10 ml C$_2$H$_5$OH) is added dropwise and with stirring to a solution of 2,6-pyridinedicarbaldehyde (1.35 g, 0.01 mole) and zinc triflate (3.63 g, 0.01 mole) in 25 ml of C$_2$H$_5$OH and 25 ml of H$_2$O during 15 mn.

NaBr (5.5 g) is added to the reaction mixture. The mixture is stirred for 4 hours during which the product precipitates. The product is recovered by filtration at a waterpump and is dried in a vacuum at room temperature for 12 hours. The product obtained (1.03 g, 1.7 mmole) is dissolved in 50 ml of methanol while NaBH$_4$ (0.48 g, 13 mmoles) is added slowly.

After stirring has been maintained for 40 mn, a further addition of NaBH$_4$ (0.44 g, 12 mmoles) is made.

After being stirred for 2 hours at room temperature, the mixture is evaporated to dryness under reduced pressure and the residue (a mixture of whitish solids) is extracted four times with 25 ml aliquots of CHCl$_3$. The pooled chloroform extracts are filtered and evaporated under reduced pressure to give a cream coloured solid.

The solid is dissolved in methanol (60 ml) and HBr (about 3 ml of a 48% aqueous solution) is added dropwise to the stirred solution to precipitate the product from the acidic medium as a pale yellow solid.

The product is recovered by filtration at a waterpump and is dried in a vacuum at room temperature.

Yield: 0.52 g, 63%.

$^1$H NMR in D$_2$O: 7.93 ppm (triplet, area 1), 7.50 ppm (doublet, area 2), 4.47 ppm (singlet, area 4), 3.05–3.35 ppm (multiplet, area 8), 2.25 ppm (multiplet, area 4).

EXAMPLE 15

Preparation of the compound of formula:

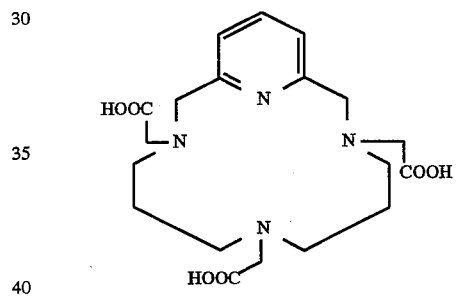

This compound is prepared by reaction with bromoacetic acid in the presence of NaOH according to the procedure described in example 5 above.

Similarly, the gadolinium complexes of the ligands corresponding to the examples 10 and 15 are prepared in the presence of a stoichiometric amount of Gd$_2$O$_3$ in aqueous medium according to the procedure described in example 8.

What is claimed is:

1. Method for in vivo imaging by nuclear magnetic resonance or X-rays, comprising the steps of administering to a human or an animal an effective amount of a diagnostic composition and subjecting the animal or human to a magnetic field or X-rays; said diagnostic composition comprising an effective amount of a neutral or anionic, mono- or polymetallic complex formed by:

1) a ligand of formula

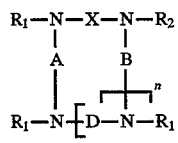

in which:

a) A and B each represents independently a linear or branched C$_1$–C$_8$ alkylene group, a linear or branched $C_1$–$C_8$ hydroxyalkylene group, a linear or branched $C_1$–$C_8$ polyhydroxyalkylene group, a —($CH_2$—$CH_2$—O)$_z$—$CH_2$—$CH_2$— group, z being an integer from 1 to 3, or a group of formula

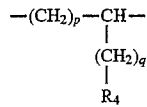

i) p being equal to an integer from 1 to 7,
ii) q being equal to an integer from 0 to 8, and
iii) $R_4$ representing
 aa) a group for the binding of the macrocycle of formula I to a biomolecule or a polymer, or
 bb) a group of formula

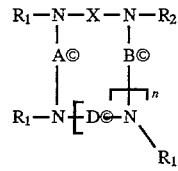

in which one of A', B', and D' denotes

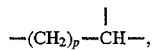

p being previously defined, and two of A', B', and D' are two of A, B and D, respectively,
b) n is 1,
c) D is X,
d) X is selected from the group consisting of

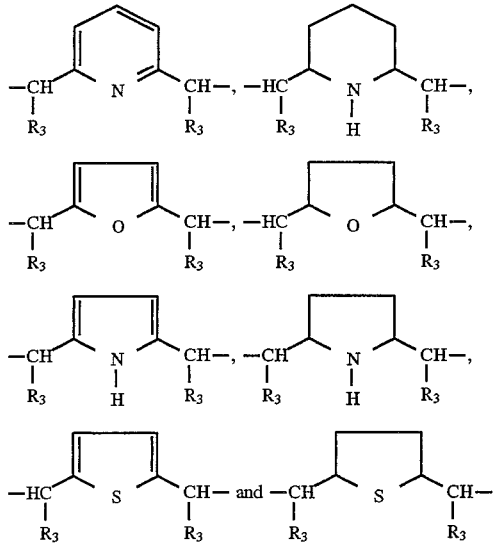

in which $R_3$ is selected from the group consisting of hydrogen, $C_1$–$C_5$ alkyl, $C_1$–$C_5$ hydroxyalkyl and $C_1$–$C_5$ polyhydroxyalkyl,
e) $R_1$ is selected from the group consisting of —$CH_2$—COOH and —$CH_2$—$PO_3H_2$ and the corresponding anions —$CH_2$—COO$^-$ and —$CH_2$—$PO_3^-$,
f) $R_2$ is selected from the group consisting of hydrogen, $C_1$–$C_4$ alkyl, $C_1$–$C_4$ hydroxyalkyl, $C_1$–$C_4$ polyhydroxyalkyl, —$CH_2$—COOH, —$CH_2$—$PO_3H_2$, —$CH_2COO^-$, —$CH_2PO_3^-$, a group

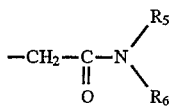

in which $R_5$ and $R_6$ is each independently selected from the group consisting of hydrogen, $C_1$–$C_4$ alkyl, $C_1$–$C_4$ hydroxyalkyl, and $C_1$–$C_4$ polyhydroxyalkyl, and a group

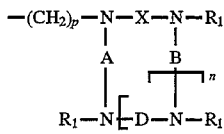

X, A, B, D, $R_1$, n and p being as previously defined; and 2) a metal ion selected from the group consisting of $Gd^{3+}$, $Mn^{2+}$, $Fe^{3+}$, $Dy^{3+}$, $Ho^{3+}$, $Tb^{3+}$, $Er^{3+}$, $En^{3+}$, $Pr^{3+}$, $Yb^{3+}$, $Pb^{3+}$, $Ce^{3+}$, $La^{3+}$, $Bi^{2+}$, and $Ba^{2+}$;

or a salt of said complex with a pharmaceutically acceptable mineral or organic base or a basic amino acid.

2. Method for in vivo imaging by nuclear magnetic resonance or X-rays, comprising the steps of administering to a human or an animal an effective amount of a diagnostic composition and subjecting the animal or human to a magnetic field or X-rays; said diagnostic composition comprising an effective amount of a neutral or anionic, mono- or polymetallic complex formed by:

1) a ligand of formula:

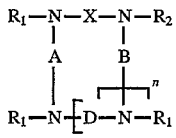

in which:
a) A represents a linear or branched $C_2$–$C_5$ alkylene group,
b) B represents a linear or branched $C_2$–$C_5$ alkylene group,
c) n is 1,
d) D is X,
e) X is selected from the group consisting of

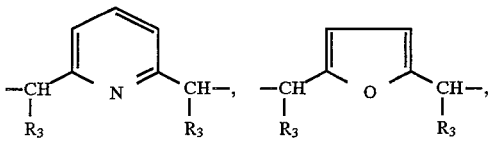

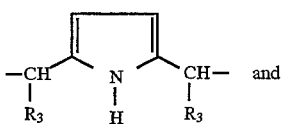

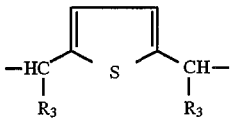

in which $R_3$ is selected from the group consisting of hydrogen and a $C_1$–$C_3$ alkyl group, f) $R_1$ is selected from the group consisting of —$CH_2$—COOH and —$CH_2$—$PO_3H_2$, and g) $R_2$ is selected from the group consisting of hydrogen, $C_1$-$C_4$ alkyl, $C_2$-$C_4$ hydroxyalkyl, —$CH_2$—COOH, and —$CH_2CO_3H_2$; and 2) a metal ion selected from the group consisting of $Gd^{3+}$, $Mn^{2+}$, $Fe^{3+}$, $Dy^{3+}$, $Ho^{3+}$, $Tb^{3+}$, $Er^{3+}$, $En^{3+}$, $Pr^{3+}$, $Yb^{3+}$, $Pb^{3+}$, $Ce^{3+}$, $La^{3+}$, $Bi^{2+}$, and $Ba^{2+}$;

or a salt of said complex with a pharmaceutically acceptable mineral or organic base or a basic amino acid.

3. Method according to claim 1, wherein in the ligand of formula I $R_4$ is selected from the group consisting of —$NH_2$, —$CO_2H$,

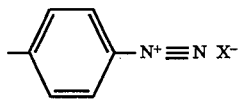

$X^-$ representing a monovalent anion $Cl^-$ or $BF_4^-$,

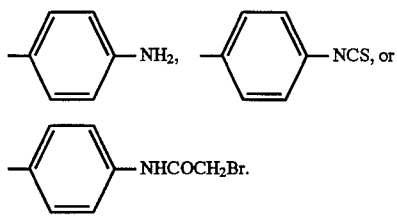

4. Method according to claim 2, wherein in the ligand of formula I $R_4$ is selected from the group consisting of —$NH_2$, —$CO_2H$,

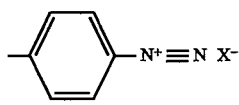

$X^-$ representing a monovalent anion $Cl^-$ or $BF_4^-$,

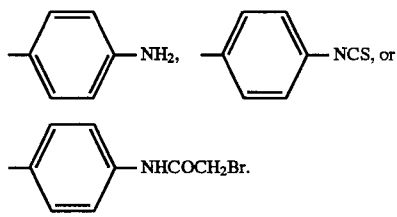

5. Method according to claim 1, wherein in the ligand of formula I A and B are identical and selected from the group consisting of ethylene and n-propylene, n is equal to 1, X and D are identical and selected from the group consisting of:

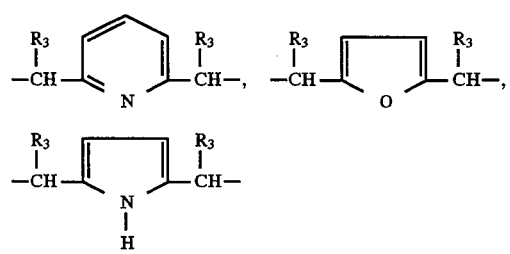

$R_3$ being selected from the group consisting of hydrogen and methyl, and $R_1$ and $R_2$ represent —$CH_2$—$CO_2H$.

6. Method according to claim 2, wherein in the ligand of formula I A and B are identical and selected from the group consisting of ethylene and n-propylene, n is equal to 1, X and D are identical and selected from the group consisting of:

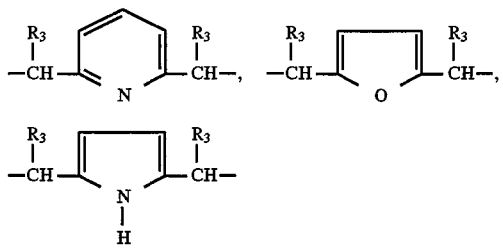

$R_3$ being selected from the group consisting of hydrogen and methyl, and $R_1$ and $R_2$ represent —$CH_2$—$CO_2H$.

7. Method according to claim 1, wherein in the ligand of formula I A and B represent a —$CH_2$—$CH_2$— group, X and D represent the group:

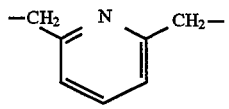

and $R_1$ and $R_2$ represent the —$CH_2$—COOH group.

8. Method according to claim 2, wherein in the ligand of formula I A and B represent a —$CH_2$—$CH_2$— group, X and D represent the group:

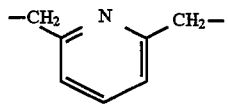

and $R_1$ and $R_2$ represent the —$CH_2$—COOH group.

9. Method according to claim 1, wherein in the ligand of formula I A and B represent a —$CH_2$—$CH_2$— group, X and D represent the group:

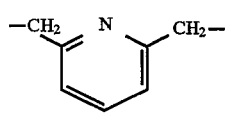

$R_1$ represents the —$CH_2$—COOH group and $R_2$ represents hydrogen.

10. Method according to claim 2, wherein in the ligand of formula I A and B represent a —$CH_2$—$CH_2$— group, X and D represent the group:

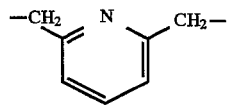

$R_1$ represents the —$CH_2$—COOH group and $R_2$ represents hydrogen.

11. Method according to claim 1, wherein in the ligand of formula I A and B represent the —$CH_2$—$CH_2$— group, X and D represent the group:

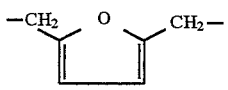

and $R_1$ and $R_2$ represent the —$CH_2$—COOH group.

12. Method according to claim 2, wherein in the ligand of formula I A and B represent the —$CH_2$—$CH_2$— group, X and D represent the group:

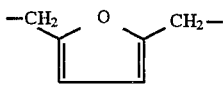

and $R_1$ and $R_2$ represent the —$CH_2$—COOH group.

13. Method according to claim 1, wherein in the ligand of formula I A and B represent the —$(CH_2)_3$— group, X and D represent the group:

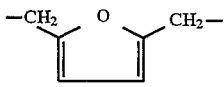

and $R_1$ and $R_2$ represent the —$CH_2$—COOH group.

14. Method according to claim 2, wherein in the ligand of formula I A and B represent the —$(CH_2)_3$— group, X and D represent the group:

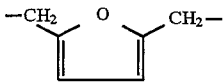

and $R_1$ and $R_2$ represent the —$CH_2$—COOH group.

15. Method according to claim 1, wherein in the ligand of formula I A and B represent the —$CH_2$—$CH_2$— group, X and D represent the group:

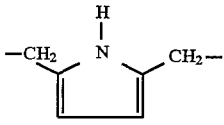

and $R_1$ and $R_2$ represent the —$CH_2$—COOH group.

16. Method according to claim 2, wherein in the ligand of formula I A and B represent the —$CH_2$—$CH_2$— group, X and D represent the group:

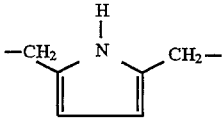

and $R_1$ and $R_2$ represent the —$CH_2$—COOH group.

17. Method according to claim 1, wherein the composition comprises a mono- and bimetallic complex in which the metal ion is selected from the group consisting of gadolinium, europium, dysprosium, iron ($Fe^{3+}$), manganese ($Mn^{2+}$) and barium.

18. Method according to claim 2, wherein the composition comprises a mono- and bimetallic complex in which the metal ion is selected from the group consisting of gadolinium, europium, dysprosium, iron ($Fe^{3+}$), manganese ($Mn^{2+}$) and barium.

19. Method according to claim 1, wherein the composition comprises a bimetallic complex formed with a ligand of formula I in which X and D represent the group:

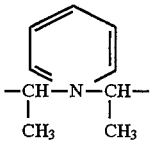

A and B represent the 2-hydroxy propylene group, and $R_1$ and $R_2$ represent —$CH_2$—$COO^-$ with two $Mn^{2+}$ ions.

20. Method according to claim 2, wherein the composition comprises a bimetallic complex formed with a ligand of formula I in which X and D represent the group:

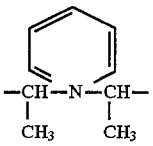

A and B represent the 2-hydroxy propylene group, and $R_1$ and $R_2$ represent —$CH_2$—$COO^-$ with two $Mn^{2+}$ ions.

21. Method according to claim 1, in which the complex is coupled to a biomolecule or a polymer.

22. Method according to claim 2, in which the complex is coupled to a biomolecule or a polymer.

23. Method according to claim 1, in which the composition is constituted by a solution of the complex in an aqueous solvent.

24. Method according to claim 2, in which the composition is constituted by a solution of the complex in an aqueous solvent.

25. Method according to claim 1, wherein the metal ion is selected from the group consisting of $Gd^{3+}$, $Mn^{2+}$ and $Fe^{3+}$.

26. Method according to claim 2, wherein the metal is selected from the group consisting of $Gd^{3+}$, $Mn^{2+}$ and $Fe^{3+}$.

27. Method according to claim 1, wherein the metal is selected from the group consisting of $Gd^{3+}$, $Er^{3+}$, $Dy^{3+}$, $Tb^{3+}$, $Ce^{3+}$, $La^{3+}$, $Br^{2+}$, $Ba^{2+}$ and $Pb^{2+}$.

* * * * *

UNITED STATES PATENT AND TRADEMARK OFFICE
CERTIFICATE OF CORRECTION

PATENT NO. : 5,645,818
DATED : July 8, 1997
INVENTOR(S) : Susan C. JACKELS and Dominique MEYER It is certified that error appears in the above-identified patent and that said Letters Patent is hereby corrected as shown below:

On the cover sheet item number "[73]", please delete "; Wake Forest University, Winston-Salem, N.C."--insert as assignee: Guerbet S.A., Villepinte, France--

Signed and Sealed this

Third Day of November, 1998

*Attest:*

BRUCE LEHMAN

*Attesting Officer*   Commissioner of Patents and Trademarks